(12) United States Patent
Wyatt

(10) Patent No.: US 7,294,513 B2
(45) Date of Patent: Nov. 13, 2007

(54) METHOD AND APPARATUS FOR CHARACTERIZING SOLUTIONS OF SMALL PARTICLES

(75) Inventor: Philip J. Wyatt, Santa Barbara, CA (US)

(73) Assignee: Wyatt Technology Corporation, Santa Barbara, CA (US)

( * ) Notice: Subject to any disclaimer, the term of this patent is extended or adjusted under 35 U.S.C. 154(b) by 0 days.

(21) Appl. No.: 11/707,835

(22) Filed: Feb. 16, 2007

(65) Prior Publication Data

US 2007/0155017 A1 Jul. 5, 2007

Related U.S. Application Data

(63) Continuation-in-part of application No. 10/600,781, filed on Jun. 19, 2003, now abandoned, which is a continuation-in-part of application No. 10/202,777, filed on Jul. 24, 2002.

(51) Int. Cl.
*G01N 9/30* (2006.01)
*G01N 33/48* (2006.01)
*G01N 21/51* (2006.01)
*G01N 15/05* (2006.01)
*B04B 5/10* (2006.01)

(52) U.S. Cl. ............ 436/45; 73/61.65; 73/61.66; 73/61.69; 356/338; 356/340; 356/343; 422/64; 422/72; 422/73; 422/82.05; 422/82.09; 436/63; 436/70; 436/86; 436/166; 436/177; 494/10; 494/16

(58) Field of Classification Search .... 73/61.65–61.66, 73/61.69, 865.5; 356/338, 340, 343; 422/64, 422/72–73, 82.05, 82.09; 436/43, 45, 63, 436/70, 86, 165, 177; 494/10, 16
See application file for complete search history.

(56) References Cited

U.S. PATENT DOCUMENTS 3,009,388 A * 11/1961 Polanyi ................ 356/40

(Continued)

FOREIGN PATENT DOCUMENTS

EP 362733 * 4/1990

OTHER PUBLICATIONS

Burtis, C. A. et al, Clinical Chemistry 1972, 18, 753-761.*

(Continued)

*Primary Examiner*—Arlen Soderquist
(74) *Attorney, Agent, or Firm*—Philip J. Wyatt

(57) ABSTRACT

A method and apparatus is described by which means molecules in suspension may be characterized in terms of the size and mass distributions present. As a sample solution is separated by centrifugal means, it is illuminated at a particular radial distance from the axis of rotation by a fine, preferably monochromatic, light beam. Despite the high resolution of such devices, a key problem associated with most separators based upon use of centrifugal forces is the difficulty in deriving the absolute size and/or molar mass of the separating molecules. By integrating means to detect light scattered, over a range of scattering angles, from samples undergoing centrifugal separation, molecular sizes in the sub-micrometer range may be derived, even in the presence of diffusion. Adding a second light beam at a displaced rotational angle, preferably of an ultraviolet wavelength, that intersects the sample at the same radial region as the first beam permits determination of the molecular concentration at that region. Combining the light scattering data with the associated concentration permits the determination of the associated molar mass. In a preferred embodiment, the light beam and detectors may be controlled to scan synchronously the sample radially during separation.

13 Claims, 8 Drawing Sheets

U.S. PATENT DOCUMENTS

| | | | | | |
|---|---|---|---|---|---|
| 3,470,381 | A | * | 9/1969 | Boyd | 250/565 |
| 3,624,835 | A | * | 11/1971 | Wyatt | 356/343 |
| 3,679,367 | A | * | 7/1972 | Negersmith et al. | 422/72 |
| 3,684,450 | A | * | 8/1972 | Alder et al. | 436/45 |
| 3,770,351 | A | * | 11/1973 | Wyatt | 356/336 |
| 4,055,076 | A | * | 10/1977 | Tropea | 73/61.66 |
| 4,084,902 | A | * | 4/1978 | Green | 356/38 |
| 4,128,400 | A | * | 12/1978 | Muhlbock et al. | 422/101 |
| 4,311,039 | A | * | 1/1982 | Koehler et al. | 73/61.69 |
| 4,348,107 | A | * | 9/1982 | Leif | 356/72 |
| 4,409,820 | A | * | 10/1983 | Nash | 73/61.64 |
| 4,457,624 | A | * | 7/1984 | Goldberg et al. | 356/336 |
| 4,478,073 | A | * | 10/1984 | Holsworth et al. | 73/61.66 |
| 4,567,373 | A | * | 1/1986 | O'Meara et al. | 250/573 |
| 4,652,137 | A | * | 3/1987 | Calzi | 356/427 |
| 4,672,216 | A | * | 6/1987 | Pitt et al. | 250/574 |
| 4,683,579 | A | * | 7/1987 | Wardlaw | 377/11 |
| 4,722,606 | A | * | 2/1988 | Bonfiglio et al. | 356/414 |
| 4,728,190 | A | * | 3/1988 | Knollenberg | 356/336 |
| 4,871,248 | A | | 10/1989 | Hoffman | |
| 5,171,995 | A | * | 12/1992 | Gast et al. | 250/339.08 |
| 5,279,150 | A | * | 1/1994 | Katzer et al. | 73/61.66 |
| 5,309,216 | A | * | 5/1994 | Weichert | 356/335 |
| 5,325,172 | A | * | 6/1994 | Kataoka et al. | 356/484 |
| 5,786,898 | A | | 7/1998 | Fitzpatrick | |
| 6,238,911 | B1 | * | 5/2001 | Kasahara | 435/288.4 |
| 6,278,518 | B1 | * | 8/2001 | Schrof et al. | 356/318 |
| 6,506,344 | B1 | * | 1/2003 | Fickenscher et al. | 422/72 |
| 6,573,992 | B1 | * | 6/2003 | Drake | 356/338 |
| 6,646,742 | B1 | * | 11/2003 | Gangstead et al. | 356/342 |
| 6,651,009 | B1 | | 11/2003 | Trainoff et al. | |
| 6,774,994 | B1 | | 8/2004 | Wyatt et al. | |

OTHER PUBLICATIONS

Tiffany, T. O. et al, Clinical Chemistry 1974, 20, 1055-1061.*
Buffone, G. J. et al, Analytical Chemistry 1974, 46, 2047-2049.*
Buffone, G. J. et al, Clinical Chemistry 1975, 21, 1735-1746.*
Mallove, E. F. et al, Journal of Aerosol Science 1976, 7, 409-423.*
Hills, L. P. et al, Clinical Chemistry, 1980, 26, 1459-1466.*
Berkowitz, S. A. et al, Biochemistry 1980, 19, 2696-2702.*
Schleicher, A. et al, Journal of Biochemical and Biophysical Methods 1983, 8, 227-237.*
Amra, C. et al, Applied Optics 1993,32,5462-5474.*
Egelhaaf, S. U. et al, Review of Scientific Instruments 1996, 67, 540-545.*
P. J. Wyatt, "Submicrometer particle sizing by multiangle light scattering following fractionation", J. Colloid and Interface Science, 1998, pp. 9-20, V. 197, Academic Press.
J. C. Giddings, "Field-flow fractionation: Analysis of macromolecular colloidal, and particulate materials," Science, 1993, 1456-1465, V. 260, AAAS.
D. T. Phillips, et.al., "Measurement of the lorenz-Mie scattering of a single particle: polystyrene latex," J. Colloid and Interface Science, 1970, 159-162, V. 34, Acad. Press.
P.J. Wyatt, "Cell wall thickness, size distribution, refractive index ratio and dry weight content of living bacteria (*Staphylococcus aureus*)",Nature, 1970, pp. 277-279 V. 226.
P.J. Wyatt, "Dielectric structure of spores from differential light scattering," Spores V, 1972, pp. 61-67, American Society for Microbiology.
P. J. Wyatt, "Structure of single bacteria from light scattering," Journal of Theoretical Biology, 1972, pp. 493-501, V. 37, Elsevier.
P.J. Wyatt, "Some chemical, physical, and optical properties of fly ash particles," Applied Optics, 1980, pp. 975-983, Optical Society of America.
D.W. Shortt, et.al., "Absolute measurement of diamter distributions of particles using a multiangle light scattering photometer. . . ," American Laboratory, Nov. 1996, pp. 21-28.
P.J. Wyatt, "Submicrometer particle sizing by multiangle light scattering following fractionation," J. Colloid & Interface Science, 1998, pp. 9-20, V. 197, Academic Press.
P.J. Wyatt, "Light scattering and the absolute characterization of macromolecules," Analytica Chimica Acta, 1993, pp. 1-40, V. 272, Elsevier Science Publishers, Amsterdam.

* cited by examiner

METHOD AND APPARATUS FOR CHARACTERIZING SOLUTIONS OF SMALL PARTICLES

RELATED APPLICATIONS AND PATENTS

This is a continuation-in-part of application Ser. No. 10/600,781 filed 19 Jun. 2003 now abandoned, itself a continuation-in-part of application Ser. No. 10/202,777 filed 24 Jul. 2002.

The following patents and applications relate to the methods of light scattering for the measurement of molecular and particle mass and size.

P. J. Wyatt, U.S. Pat. No. 6,411,383 B1 (25 Jun. 2002) "Method for measuring the $2^{nd}$ virial coefficient."

S. Trainoff and P. J. Wyatt, U.S. Pat. No. 6,651,009 B1 (18 Nov. 2003) "Method for determining average solution properties of macromolecules by the injection method."

DEFINITIONS

The term "particle" as used herein shall include molecules such as proteins, protein conjugates, and protein complexes, as well as viruses, nano particles including nanotubes, and all small particles of size less than about 100 micrometers.

BACKGROUND

The characterization of small particles in terms of their properties such as size, mass, shape, as well as the associated distributions of these quantities within a sample solution, has long represented a major objective of a broad range of analytical instruments. Light scattering instrumentation plays a major role among them as the technique is absolute and does not require calibration standards. This is especially true for very small particles such as molecules, viruses, and other classes of nano-particles. A light scattering measurement of a polydisperse molecular solution will yield a weight average molar mass provided that the molecular or particle concentration is known or determined by measurement. For particles/molecules of size greater than about 20 nm, the mean square radius of the scattering particles may be derived from the measured variation of the scattered light intensity with scattering angle.

The ability to measure the distributions of mass and size present in the scattering sample has been of particular importance. In order to determine these distributions, it is necessary to separate the particles present so that the scattering properties and concentration of each separated species present may be measured separately. This separation has been achieved traditionally by processes referred to as chromatographic separation. The combination of multiangle light scattering, MALS, with chromatographic separation and concentration measurement permits the immediate determination of these distributions.

Several separation techniques have been developed for such chromatographic purposes. Foremost among them is size exclusion chromatography, SEC, which is based upon forcing the solutions through columns packed with a material causing particles/molecules of larger size to transit the column more rapidly than the smaller particles. The latter are able to penetrate deeper into the interstices of the packing matrix and spending, therefore more time therein than their larger companions.

Other frequently used separation techniques include various forms of field flow fractionation, FFF, devices add reversed phase chromatography columns. For a large range of particle/molecular sizes, few separation techniques are as effective as those provided by centrifuges in their various implementations. With the exception of the analytical ultracentrifuge, AUC, such devices cannot produce a measure of mass or size without resort to calibration standards of some type. Even the AUC, when used to deduce the mass distributions of molecular solutions, requires a considerable number of ancillary measurements as well as some assumptions concerning the particles themselves such as density and shape. Operation and interpretation of the AUC instrumentation and results requires operators with exceptional training and skills. The object of the invention described here is to establish a method and apparatus by which centrifugal devices may be used to measure, in an absolute sense, many of the properties of molecular and particle suspensions. Another objective of the invention is to simplify the subsequent analyses associated with a centrifugal separation. Still a further objective of this invention is to be able to extract more information about the separating samples achieved by the centrifugal separation processes than has heretofore been possible.

Of all the devices that may be used for measuring the sizes of particles in the nanometer range, the disk and ultra centrifuges are among those most capable of providing high-resolution separations. Despite such resolution capability, the operation of such centrifuges is generally fraught with considerable ambiguities. Most of these problems are associated with uncertainties in the derived sizes of particles since such sizes are based entirely upon the arrival times of the separated particles at a detector. By using a mixture of the unknown sample particles with particles whose sizes are precisely known, these arrival times may be calibrated to some extent. Unfortunately, despite such calibrations, small variations in temperature and rotor speed, in addition to so-called streaming phenomena, often render such calibrations questionable. Another major difficulty relates to the need to know precisely the density of the particles and that of the fluid environment in which the separation is performed. Virtually all subsequent analyses are based on the a priori assumption that the particles so-separated are homogeneous spheres. Whenever a gradient is used, its explicit density variation should be known as well. Other problems associated with determining particle size by measuring times-of-arrival at the detector include deviations of Reynolds' number in excess of 0.5%, effects of sample dispersion due to Brownian motion resulting in the spreading out of the arrival times of identical particles, band broadening dependent on the speed of separation, establishing suitable gradients to prevent streaming, overloading sample concentration, range of particle sizes in the sample, problems with deconvolution analyses, etc. Virtually all these difficulties are associated with one basic shortcoming of these devices: centrifugal separation is not an absolute measurement method for most classes of particles. In other words, with the exception of a theoretical arrival time for homogeneous spheres at the detector, once a set of particles has arrived, their size cannot be measured directly. Of course, if the particles are not homogeneous spheres, i. e. of unknown structure, even the best of prior calibration procedures can result in great uncertainties in interpretation. Centrifugal separation would appear ideally suited for the subsequent application of a multiangle light scattering, or MALS, analysis were it not for the inaccessibility of the samples. Thus, using cross flow field flow fractionation as described by Wyatt, for example, in his 1998 article "Submicrometer particle sizing by multiangle light scattering following fractionation," that appeared in *J. Colloid and Interface Science* volume 197, pages 9-20, multiangle light scattering analyses of the eluant samples following separation produces detailed and accurate size and distribution information. The concept has been applied also to the analyses of samples separated by other methods including size exclusion chromatography and capillary hydrodynamic fractionation, to name a few. A centrifugal device with an accessible eluting sample following separation was developed by J. Calvin Giddings and is referred to as sedimentation field flow fractionation, or SdFFF for short. This method, described, for example by Giddings in his 1993 paper in volume 260 of *Science* at pages 1456 et seq., required an elaborate set of slip rings and capillaries. Other types of FFF separation techniques are also discussed in Giddings' paper. Combined with a sequential MALS measurement, the analysis of eluting samples permitted the accurate characterization of each eluting fraction of particles independent of diffusion effects. Nevertheless, the SdFFF device had neither the resolution nor dynamic range of the more conventional centrifugal separation devices and was prone to leaks within a short time of installing new seals.

Results derived from the more conventional disk centrifuge and analytical centrifuge devices are based on the optical examination of small regions within the sample volume being subjected to centrifugal forces. Remote light sources, i. e. stationary relative to the spinning samples, are synchronized to the radial motion of the sample through the incident light beam to yield some measure of particle presence in the particular region being "interrogated." Such transmitted light beam measurements may include absorption and forward scattering measurements as well as fluorescence characteristic of some types of samples. From such measurements, further attempts are usually made to derive a size distribution of the particles present in the sample by interpreting the scattering and/or obscuration of the transmitted light beam at the detector in terms of Lorenz-Mie scattering theory, i. e. assuming the particles are homogeneous spheres. The forward-scattered light intensity is assumed to arise because such spheres of a known radius, $\alpha$, have entered the incident light beam. However, such "known" size was extracted from the time of arrival of the particles based on the relation $$D \approx \frac{\sqrt{18\eta \ln(R/R_0)}}{\omega(\rho_p - \rho_f)^{\frac{1}{2}} t^{\frac{1}{2}}}, \quad (1)$$

where $D=2\alpha$ is the particle diameter, $\omega$ the angular velocity of the rotor, $R_0$ is the radius at which the sample particles were injected at time $t=0$, $R$ is the radius at which they are detected, $\eta$ is the fluid viscosity, and $\rho_p$ and $\rho_f$ are the particle and fluid specific gravities, respectively. Possible sources of error in the terms of Eq. (1) can be significant. Most importantly, Eq. (1) only applies strictly for the case of homogeneous spherical structures. In addition, the fluid density must be known at the particular temperature at which the separation is being made. For centrifugal devices operating in air, the frictional forces at such high speeds generally result in the production of an increased temperature of the sample during separation and, thereby, a decrease of the fluid density, $\rho_f$.

Perhaps the greatest source of error in deriving particle size from Eq. (1) occurs when the particle density is close to that of the medium which is the case, for example, for proteins and a variety of particles produced by emulsion polymerization. When $\rho_p$ and $\rho_f$ are very close, slight errors in $\rho_p$ can result in significant errors in the derived particle diameter, D. In addition, of course, Eq. (1) applies only to spherical particles. For non-spherical particles, the hydrodynamic radius, $r_h$, derived is just that of an equivalent sphere. It is another objective of this invention to provide a means by which the hydrodynamic radius of a particle passing through the detection beam may be determined far more accurately and without reference to a known particle standard, often used for centrifuge calibration. In addition to a measurement of the hydrodynamic radius, a particularly useful objective of this invention is the measurement of the so-called mean square radius. Knowledge of both of these radii often permits the derivation of the particle structure as well.

It is a further objective of this invention to provide an absolute measure of the radius of a spherical particle in the range of about 10 through 1000 nm without the use of calibration particle standards. An additional objective of this invention is to permit the accurate derivation of the particle size distributions of particles separated by centrifugal means even in the presence of significant diffusion caused by Brownian motion. Another objective of this invention is to circumvent, whenever possible, distortions in derived size distributions caused by other effects that tend to broaden the separated particle bands that appear at the detector such as systematic variations in rotor speed, changes in fluid temperature and viscosity, etc. Still another objective of this invention is the ability to measure sizes and size distributions for a broad range of inhomogeneous particles whose individual density variations may not be known a priori. Because some implementations of the disk and ultracentrifuges purport to be able to measure the concentration of very small particles directly, another objective of this invention is to be able to measure the molar mass of certain classes of molecules separated by centrifugal means. The success of the present invention to achieve these objectives depends critically upon the ability to integrate a MALS detection system into a centrifugal separation device and to use the existing features of centrifugal devices to permit more accurate analyses of the measured samples. Heretofore, such integration has neither been attempted nor considered.

SUMMARY OF THE INVENTION

The present invention permits the analysis of particles separated by sedimentation methods, such as a disk centrifuge or analytical ultracentrifuge, without requiring the use of standards for calibration. Because of this capability, problems with the separation mechanisms themselves are readily detected. Most centrifugation separations and subsequent analyses are based upon measuring the intensity of a highly collimated beam of light that has passed through a sample undergoing sedimentation separation. The transmitted light beam provides a measure of the sample absorption as well as a fraction of the forward scattered signal. By correcting for the contributions of forward scattering, assuming that the particles are homogeneous spheres and using Lorenz-Mie scattering theory, and applying a size/time relation such as shown in Eq. (1), the particles' effective size is derived. Most devices that use such beam geometries, such as Koehler, et al. in their U.S. Pat. No. 4,311,039, need to collimate the light source and detector so that the detected light corresponds to that interacting with the volume containing the small fraction of particles being illuminated.

The present invention modifies the detection of light passing through the sample by adding optical elements, masks, and an array of detectors permitting, thereby, measurement of the light scattered by a well-localized sample over a range of angles. This multiangle light scattering detection device permits the determination of the scattering particles' mean square radius that, for a wide range of particle shapes, may be expressed as an effective particle size. As mentioned earlier, multiangle light scattering is often referred to by the acronym MALS. From such measurement of each fraction passing through the incident light beam, a size distribution may be derived that is absolute and independent of the time of arrival of the sample at the detector. For many types of particles in the submicrometer size range, these measurements are virtually independent of both particle density and refractive index. If the particle concentration at the region of detection is also known, the weight averaged molar mass of said particles may be determined from the detected MALS signals. Alternatively, following U.S. Pat. No. 6,774,994 by Wyatt, et al., if the particle shape and refractive index are known, the particle number densities may be determined directly from the MALS measurements.

The inventive concepts disclosed further have immediate application to other devices utilizing centrifugal forces for separation. Whereas many practitioners of such separation processes have been reliant upon the use of calibration standards as well as having to make the often overwhelmingly precise measurements of the physical parameters of the samples and fluids involved, with the present invention the entire measurement process and subsequent interpretation is simplified significantly.

DETAILED DESCRIPTION OF THE INVENTION

Figure 1:
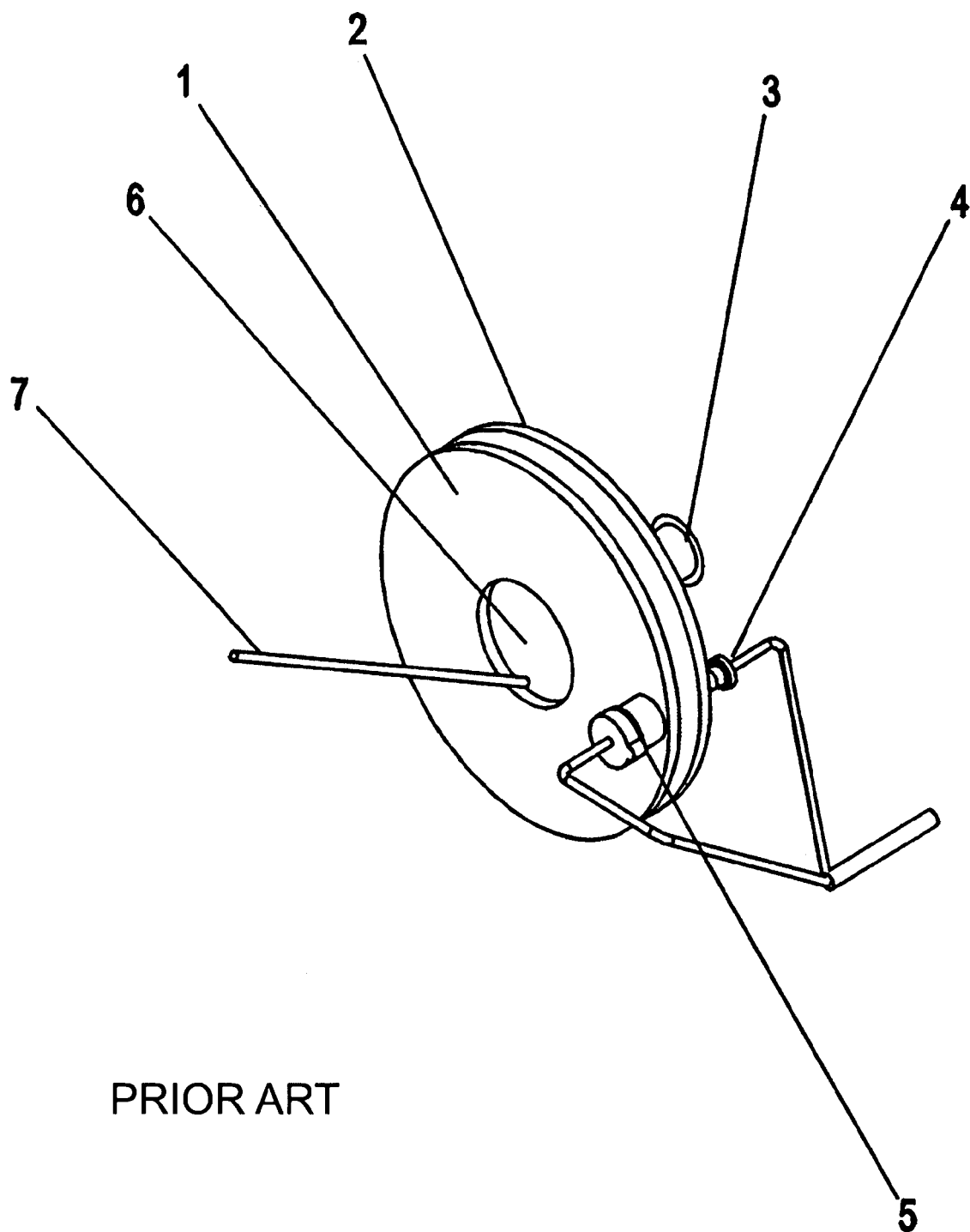
FIG. 1 shows the general structure of a disk centrifuge with transparent walls.
Figure 2:
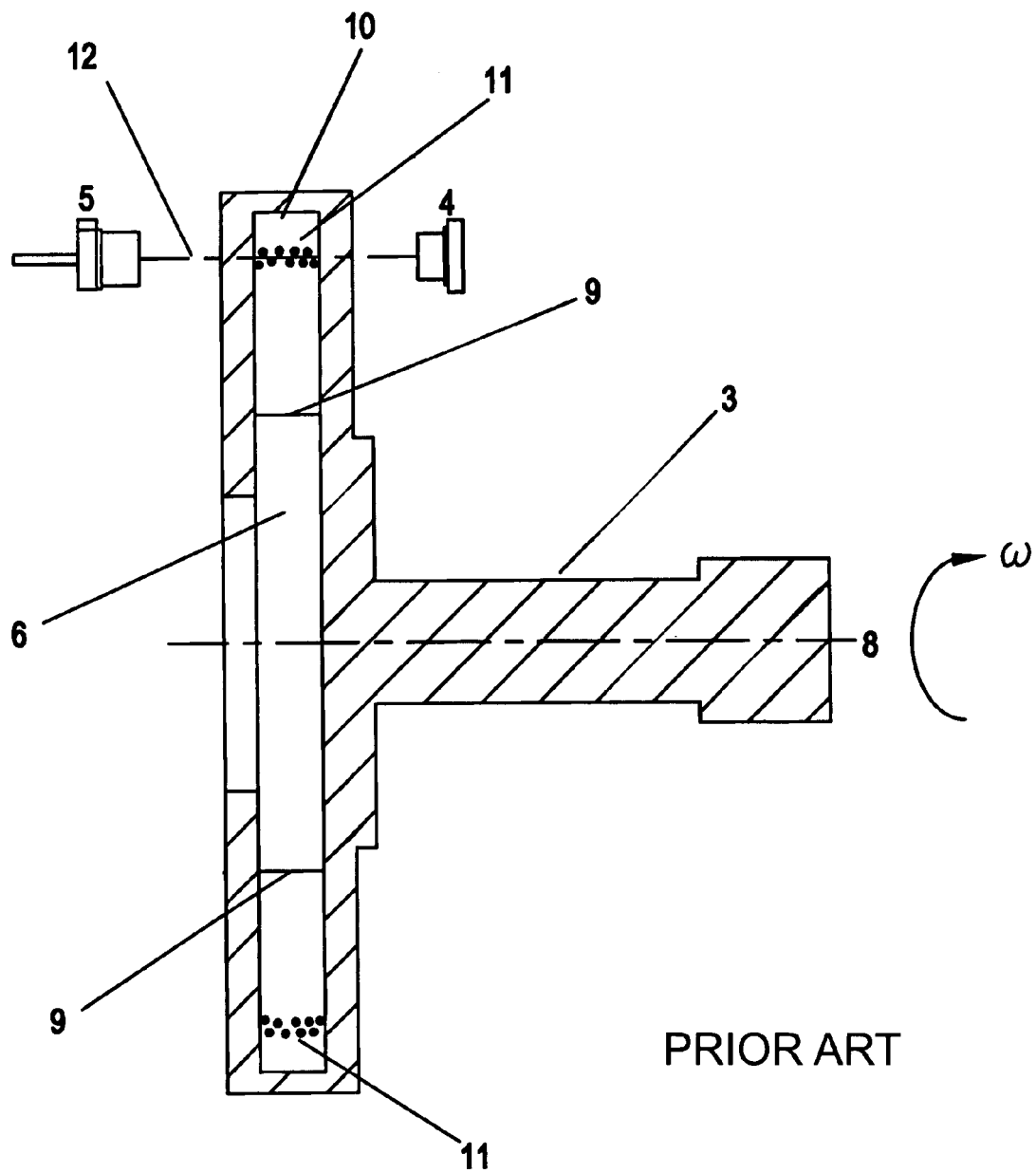
FIG. 2 shows an end-on view of a disk centrifuge indicating the liquid meniscus and the radially increasing sample band.

The typical rotor and sample containing elements of a centrifuge are shown in FIG. 1 for an embodiment corresponding to that of a disk centrifuge. These include the transparent side plates 1 and 2 forming the sides of a fluid-containing sample chamber therebetween and a central rotor hub 3 attached to one of the plates. A light source 4 producing a finely collimated light beam is shown with a detector cell 5. Samples are introduced generally through the center opening 6 of transparent side plate 1 via inlet channel 7. Such and similar structures have been disclosed, for example, in the U.S. Pat. No. 4,311,039 by Koehler et al. and U.S. Pat. No. 5,786,898 by Fitzpatrick. FIG. 2 shows an end-on view of the sample chamber during operation. The particle sample is inserted through the opening 6 concentric with the axis of rotation 8 through the rotor 3 so that it begins its separation once in contact with the fluid meniscus 9. Because of centrifugal forces, the sample migrates outwardly and eventually reaches the chamber's outermost boundary 10 where it remains until the chamber is cleaned. As each fraction of the sample reaches the detection region 11, it passes through the incident light beam 12 from source 4 that is monitored at detector 5. The light beam is generally well collimated and often monochromatic, for example, when the source a laser. On the other hand, it may be generated by a monochrometer providing a beam of controlled variable wavelength. Such monochrometers are often provided as part of the apparatus of analytical centrifuges. For certain classes of particles, a well-collimated light beam from a UV source is preferable.

The use of such centrifuges for the determination of particle size and particle size distributions, based on the type of attenuated transmitted light measurements described above, is generally referred to as the "photosedimentation method". Because the associated separation theory refers specifically to particles of spherical shape, the versatility of the method becomes extremely limited and, for most measurements, eventually requires the introduction of "calibrated" standards. The departures from both theory and interpretation of arbitrarily shaped particles are rarely discussed in the literature or the patents based upon such measurements. Although Eq. (1) is the form generally presented to show the relation between particle diameter D and arrival time t, it is instructive to examine its basis. As the chamber rotates at an angular velocity $\omega$, a particle of mass m is forced outwardly by the centrifugal force $mR\omega^2$, where R is the distance from the axis of rotation 8. However, if the particle density is $\rho_p$, the fluid density is $\rho_f$ and the particle occupies a volume V, then the centrifugal force becomes $(\rho_p-\rho_f)VR\omega^2$. For the case of a spherical particle of radius $\alpha$, the centrifugal force is simply $4\pi\alpha^2(\rho_p-\rho_f)R\omega^2/3$. Opposing the radial motion is the so-called Stokes' force which, sphere, is just $6\pi\eta\alpha\, dR/dt$ where $\alpha$ is the radius of the sphere and $\eta$ the viscosity of the fluid. Note that this latter formula applies only to a sphere and, therefore, the only result derivable in closed form. The net radial force on a spherical particle, therefore, is just the difference of the two forces, i. e.

$$m\ddot{R}=4\pi(\rho_p-\rho_f)R\omega^2\alpha^3/3-6\pi\eta\alpha\dot{R} \qquad (2)$$

or, since $m=4\pi\alpha^3(\rho_p-\rho_f)/3$, $$\ddot{R}=R\omega^2-9\eta\dot{R}/[2\alpha^2(\rho_p-\rho_f)]. \qquad (3)$$

Thus $$\ddot{R}+b\dot{R}-\omega^2 R=0. \qquad (4)$$

Equation (4) is readily solved in the general form $$R = C_1\exp(\alpha_1 t) + C_2\exp(\alpha_2 t), \qquad (5)$$

-continued where $$\alpha_{1,2} = \frac{-b \pm \sqrt{b^2 + 4\omega^2}}{2}$$

$$= -b/2 \pm \sqrt{(b/2)^2 + \omega^2},$$

and $b=9\eta/[2\alpha^2(\rho_p-\rho_f)]$. At $t=0$, $R=R_0$, the radius at which the sample is inserted. Thus $C_1+C_2=R_0$. Also $\dot{R}=0$ at $t=0$, so $C_1\alpha_1+C_2\alpha_2=0$. Combinig these initial conditions to detern-ime the coefficients $C_1$ and $C_2$ results in the final expression for the position, $R(t)$, of the spherical particle as a function of time:

$$R(t) = R_0 \exp(-bt/2)\left[\cosh\frac{b}{2}\sqrt{1+(2\omega/b)^2}\,t + \sinh\frac{b}{2}\sqrt{1+(2\omega/b)^2}\,t\right]. \quad (6)$$

For typical separations for which $\omega$ is of the order of $2\pi10^4$, where the fluid is water, the sphere is of diameter 100 nm, and the density difference berween the particle and fluid is of the order of $5\times10^{-2}$, the quantity $2\omega/b \ll 1$. Equation (6) then becomes simply $$R=R_0\exp(\omega^2 t/b) \quad (7)$$

Solving Eq. (7) for yields Eq. (1) immediately. Note that all of these results apply to spheres only and are affected considerably by even slight differences berween the actual particle and flued densities and those measured. For the case of inhomogeneous particles, even of spherically symmmet-ric shape, the average particle densities well may vary with particle size making the interpreatation of Eq. (1) even more uncertain.

The general chamber structure of the disk centrifuge per, for example, the device previously referenced by Koehler, et al. Will result in a cylinder of fluid confined berween two plates. Particles confined in such rotating fluids will be subject to both centrifugal and Coriolis forces. The Coriolis force, of magnitude $2\omega\dot{R}$ causes a motion in the direction of rotation. Since the ratio of the Coriolis force to the centrifu-gal force, $\omega^2 R$, is $2\omega/b$, we see that it is generally negligible.

Hoffman discloses an application of a disk centrifuge manufactured by Horiba, Ltd. of Kyoto, Japan, in his U.S. Pat. No. 4,871,248. The Horiba disk centrifuge, e.g. their CAPA 500, makes use of cuvettes mounted within the disk structure that rotates in a horizontal plane. These small cuvettes restrict any motion inthe direction of rotation and eliminate thereby any Coriolis effects, no matter how great the angular velocity of the system. Thus samples are placed into the cuvettes as uniform dispersions that separate into specific populations durin the spinning of the disk.

Light scattering is perhaps the best-known means for measuring the size and mass of particles. Measurement of the scattered light intensity, as a function of scattering angle can be used to deduce such size for many diverse types of particles. For the case of a spherical particle, measurent of such mutuangle light scattering patterns may be used to dirive both sphere diameter and refractive index. Phillips, Wyatt and Berkman have demonstrated this, for example, in their 1970 paper appearing in the Journal of Colloid and Interface *Science*, volume 34, pages 59 to 162. The structure of particles exhibiting spherically symmmetry may also be deduced un some cases by measurement to the determina-tion of such structures may be found in the following papers, for example:

"Cell Wall Thickness, Size Distribution, Refractive Index Ratio, and Dry Weight Content of Living Bacteria (*Staphylococcus aureus*)," Nature 226,277 (1970).

"Dielectric Structure of Spores from Differential Light Scattering," *Spores V*, American can Spcoety for Microbiology, (1971).

"Structure of Single Bacteria from Light Scattering," with D. T. Phillips, J. Theor. Biol. 37, 493 (1972).

"Some Chemical, Physical and Optical Properties of Fly Ash Particles," Applied Optics 14, 975 (1980).

For very small particles whose radii are less than about 10 nm, their size cannot be determined by MALS for incident light in the visible region. This limitation is due entirely to lack of resolution at the wavelengths used for the measure-ments. Thus MALS cannot be used to derive the size of proteins, for example, typically of the order of a few nanometers. However, since various centrifuges, such as the analytical ultracentrifuge of Beckman Instruments, are equipped with advanced absorption optical systems, they are capable in principle of measuring the absolute concentration at any point in the sample. With the MALS capability of the present invention, it is possible to derive protein molar masses directly by combining the light scattering data with the concentration results. Historically, it must be mentioned that measurements with the ultracentrifuge have been com-bined with complementary measurement techniques such as light scattering, quasielastic light scattering, and viscometry in order to understand better the traditional ultracentrifuge results when the particles or proteins of interest are not spheres.

When the refractive index of particles subject to MALS measurements is close to the refractive index of the sus-pending fluid, there are several simplifications in the theo-retical interpretation of the MALS measurements that permit the determination of the so-called root-mean-square, or rms, radius of such particles. For many simple structures such as spheres, rods, disks, ellipsoids, etc., the rms radius may be related directly to more characteristic size parameters such as radius or length. With some a priori knowledge of the particles' shape, the present invention permits, for many classes of particles, the determination of their size even though they are not spheres. In addition, for a reasonably wide range of refractive indices and corresponding densities, the sizes of even. spherical particles may be determined accurately from their measurement in a centrifugal device incorporating the key features of the present invention. As clearly evident from Eq. (1), slight errors in the determina-tion of particle density can result in large sizing errors using devices based on conventional centrifugal separations alone. The density of simple polystyrene spheres relative to water differs only of the order of $5\times10^{-2}$ and obviously any errors in this value will have a major effect on the determination of the corresponding particle size based on Eq. (1). The present invention eliminates this dependency to a great extent.

In order to make MALS measurements from a sample undergoing centrifugal separation according to the methods taught by the present invention, special optics and detector capabilities must be incorporated into the centrifugal devices.

Figure 3:
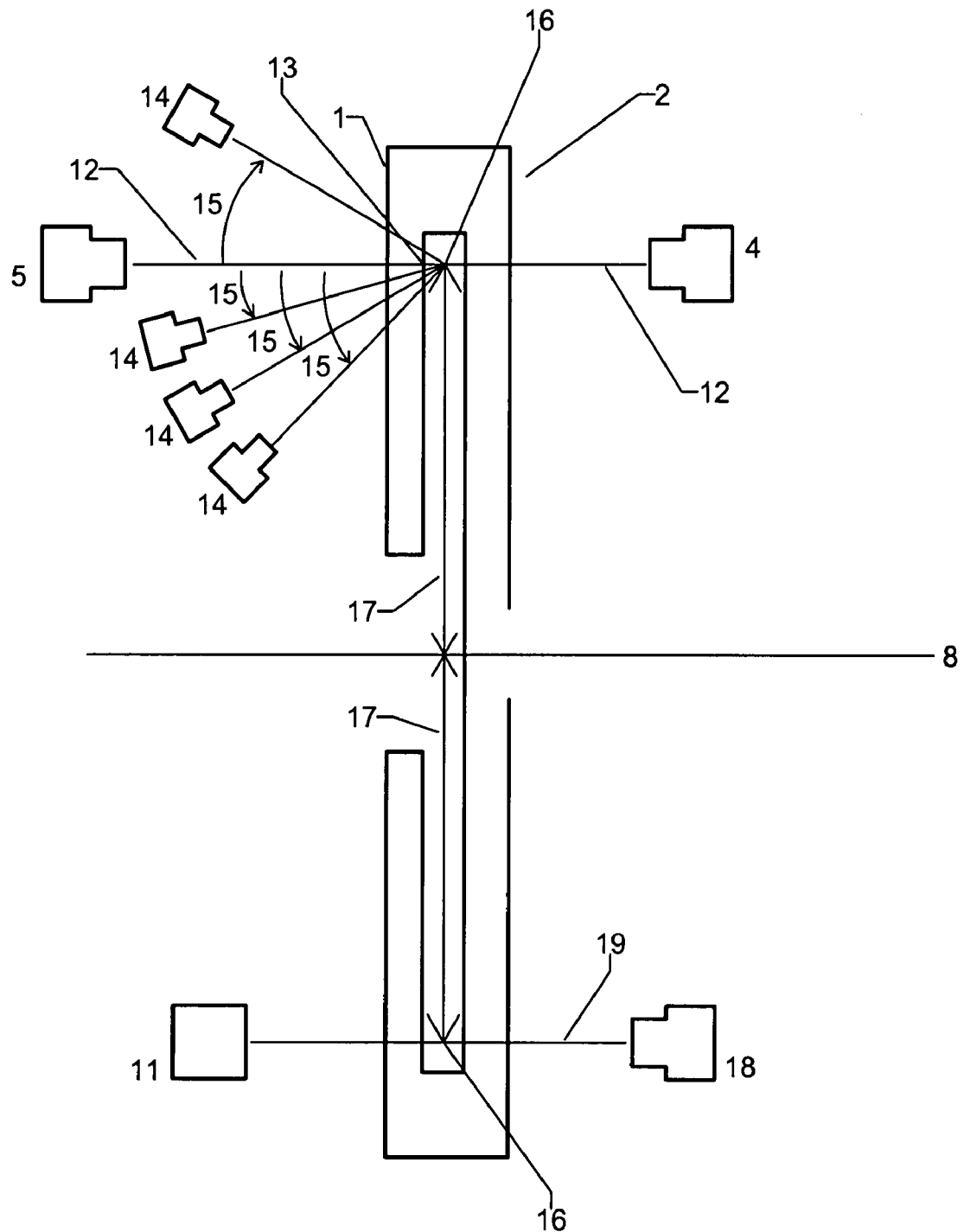
FIG. 3 shows a partial cross section of a modified disk centrifuge incorporating a set of scattered light detectors permitting the measurement of light scattered by the sample over a range of scattering angles together with a secondary light source used to provide sequential illumination of the samples.

FIG. 3 shows a section of the exemplar disk centrifuge of FIG. 2 illustrating a preferred embodiment of the invention. A finely collimated light beam 12 from light source 4 passing through the containing exterior walls 2 and 1, and exiting at 13 before entering a transmitted light detector 5.

In a preferred configuration of the device, the beam 12 enters and exits normally through the anti-reflection coated surfaces 2 and 1. Also shown is a set of highly collimated detectors 14 each receiving light scattered by the sample region 16 into unique angular directions 15 with respect to the emerging beam 12. The detectors 14 are collimated so as to accept light scattered from the sample region 16 and each subtends a small solid angle. Because the separations of particles generally span a small range of radial distances 17 with respect to the axis of rotation 8, it is essential that the detector collimation provide a high degree of sample/solute resolution with respect to the radial direction. This is achieved by collimation that provides for a highly localized coincident field of view at each distinct detector. Adding optical lenses in front of the detectors would further restrict the depth of field and, thereby, the contributing scattering volume detected. The specific masking and detector orientation required to detect light scattered from the same highly restricted scattering region adds some complexity to the apparatus. Most importantly, the efficiency of collecting scattered light is affected by internal reflections at the interfaces, as well as the passage of stray light into the detectors. In the preferred embodiment of this invention, the fine incident light beam would be from a laser source and would be plane polarized perpendicular to the plane containing the detectors 14 shown in FIG. 3. Although such co-planar detectors are sufficient to provide the characterizing data that would form the basis for subsequent analysis of the molecules/particles being measured, for some classes of measurements or because of geometrical limitations, detectors outside of such a preferred plane may be employed. Such detectors would be classified by both a scattering angle and an azimuthal angle with respect to a defined plane.

As mentioned earlier, if the concentration of the light scattering particles is known, their weight average molar mass also may be determined. Needed also, in addition to their concentration, is the quantity dn/dc, where dn is the change of the refractive index of the solution for a change of molecule/particle concentration dc. FIG. 3 also shows an additional light source 18 producing another collimated light beam 19 detected by a corresponding detector 11. This additional light beam 19, which in a preferred embodiment would be from a variable UV source 18, will intersect the plates 1 and 2 at the same radial distance 17 with respect to the axis of rotation 8 as the other finely collimated light beam 12. As the time between the intersection of the same radial region successively by the two beams 12 and 19 is generally very small, differences of the sample sequentially illuminated by these beams will be negligible. Thus the sampling by the two light sources will occur at the same sample element.

The structure shown in FIGS. 3 for the detection of scattered light from a disk centrifuge sample is quite different from the conventional transmitted beam detection shown in FIG. 1. Most importantly, the particles in the illuminated region 16 are detected by the light they scatter in addition to the more conventional absorption means achieved by monitoring the transmitted beam as implemented by the added light source 18. The forward transmitted beam 12 is measured at detector 5 which may serve also as a light trap, preventing, thereby, the presence of stray light that might be scattered by adjacent structures into the MALS detectors 14. The trap incorporated therein could consist of a Rayleigh horn or even a mirror or prism structure that would remove the incident beam and send it in a region where any light scattered from such deviated beam would not be detectable by any of the collimated detectors 14. The trap may be comprised also of an optically dense and non-reflecting medium such as anti-reflection coated black glass. However, for measurements of the intensity of the transmitted beam 12, a combination of a beam intensity detector and a beam trap will be required. Because of the refractions at the exit surface 1 of scattered light shown in FIG. 3, the angular positions of the detectors relative to the incident light beam are different than the corresponding scattering angles within the liquid medium. These differences may be easily calculated using conventional refraction geometry. It should be noted that the one or two light sources and their associated detectors may be constructed to enable them to be moved radially during the separation as shall be described in detail later in this specification. As is traditional for the analytical ultracentrifuge, these structures may be programmed to scan repeatedly in the radial direction. The integration of light source and detector structures whose radial positions may be changed during the measurement process is applicable to all centrifugal separation devices.

Figure 4A:
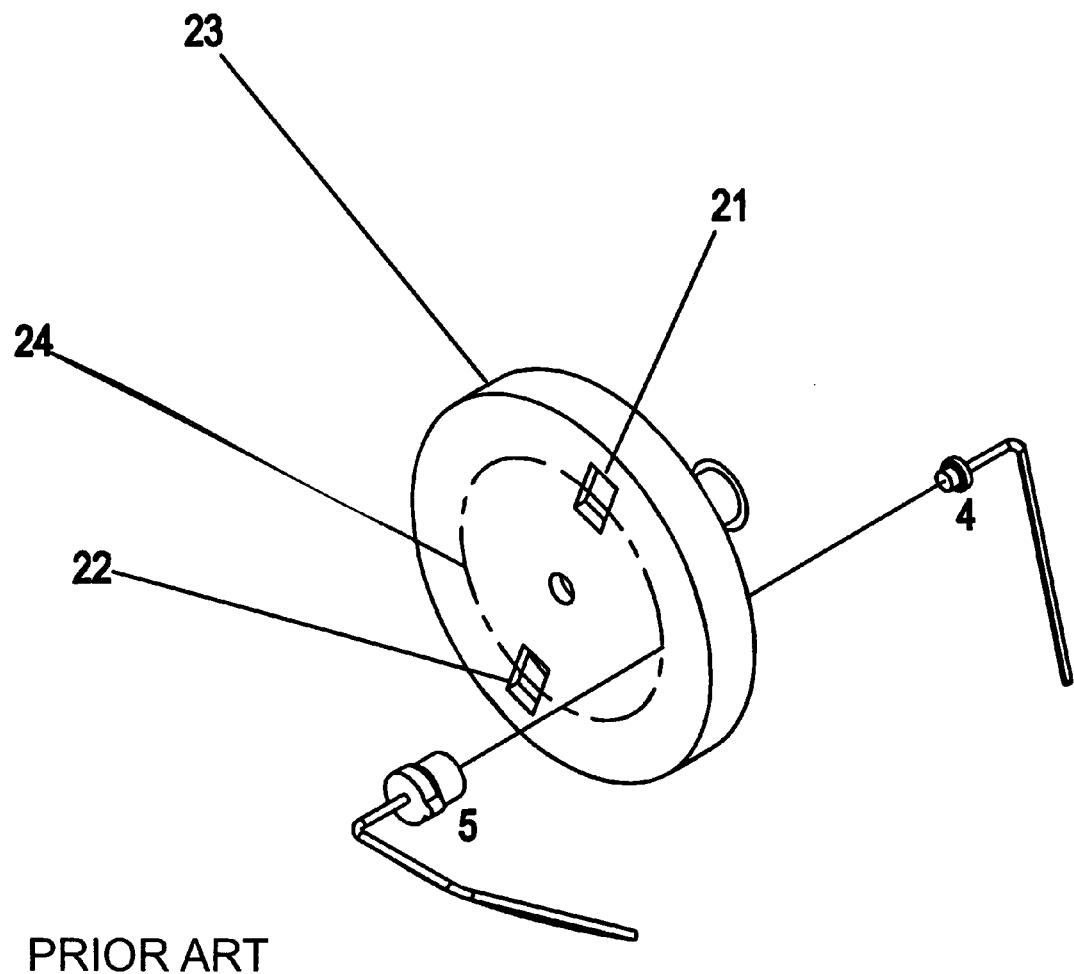
FIG. 4 corresponds to an alternate form of a disk centrifuge integrating the same illuminating and detection components of FIG. 3 but wherein the samples are contained in discrete sample cells or cuvettes.
Figure 4B:
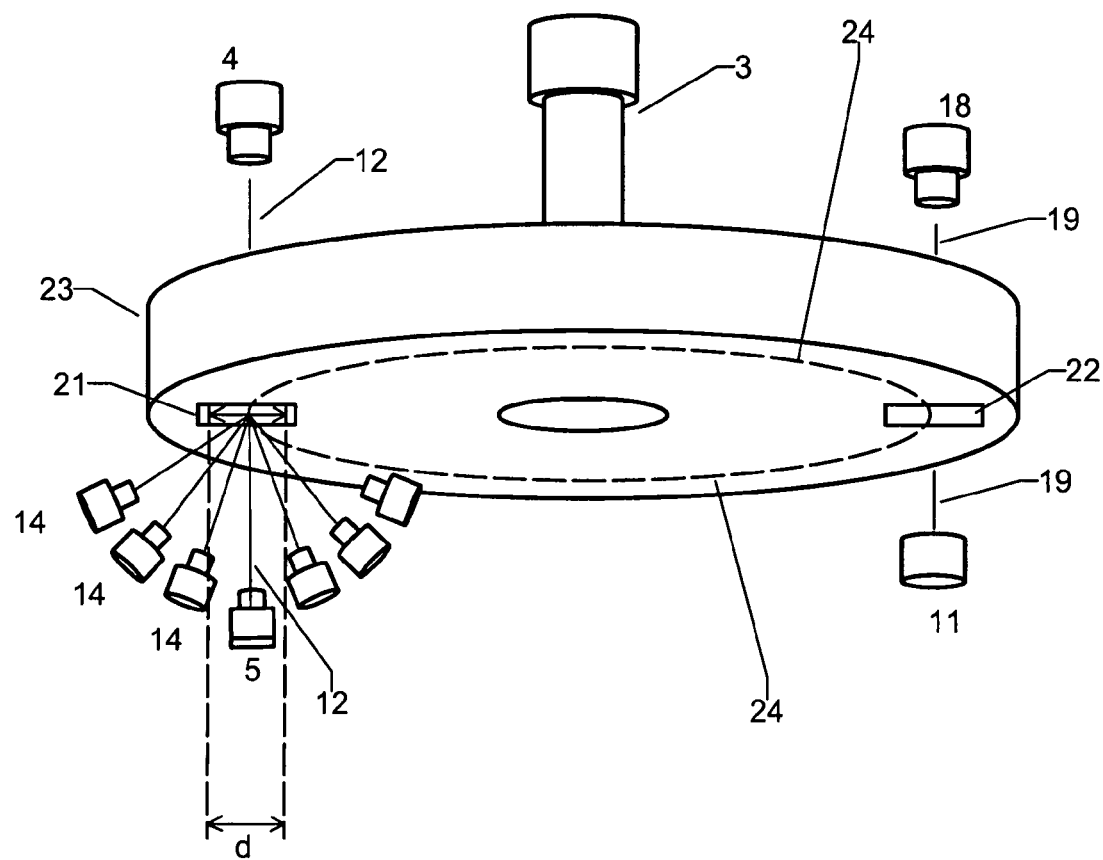

FIGS. 4a and 4b show the basic elements of the Horiba disk centrifuge mentioned earlier. Two cuvettes, containing the sample and reference fluids respectively, are placed at 21 and 22 within the horizontal disk 23 rotating about the axis 3. The light source and detector are similar to that used with the more conventional disk structure of the Koehler et al. device discussed earlier though because the cells or cuvettes, and associated samples, occupy only a small part of the circular path 24 traced out by the light source-produced beams 19 or 12 as the disk rotates. Once again, as in the case of the traditional disk centrifuge, two light sources may be provided at 4 and 18 that intersect the cuvette-holding rotor at the same radii. Light source 19 would correspond to the conventional single beam source, though in its preferred embodiment, it could operate in the UV and serve, thereby, as a concentration detector. It would detect the beam 19 transmitted through the sample and detected at 11. The second light source at 4 would be a laser in the preferred embodiment. This source would illuminate the samples passing through the beam 12 produced thereby. The transmitted laser beam 12 would be detected at 5 and the light scattered by the illuminated sample would be detected over a range of angles by the various detectors 14. Either or both light sources 4 and 18 may be operated in a modulated manner so that they are turned on only during the period the sample or reference cuvettes are in the beam. High resolution of a sedimenting sample requires that the light beam diameter be as small as practical. For the Horiba device, the beam diameter is many times greater than the 0.1 to 1 mm of currently available laser sources preferred for the present invention.

Note in FIG. 4b that the detectors 14, light trap/beam monitor 5, and source 4 are shown to be able to move together in the radial direction over a range d. The second light source 18 and detector 11 may also be constrained to move cooperatively with the elements associated with the first light source so that both beams illuminate the same sample at the same position, though there is a negligible delay between the two beams as the rotor moves the intersected sample region from one beam to the other.

Note that the inventive concept is implemented in the same manner for both types of disk centrifuges, though the light sources may be operated in slightly different manners, i. e. continuous or pulsed. The light sources of the Horiba type disk centrifuge may be operated continuously, as well. The collection interval of all detectors may be synchronized with the intersection of the source beams with the sample cuvettes. The intersection of the beams with the cuvettes may be normal or at another angle if a larger range of scattering angles is desired. It should be emphasized that in the preferred embodiment of the centrifuges with integrated MALS detectors, the second light source may be used as a concentration detector. For many types of particles with diameters greater than, say, 20 nm, their. equivalent size may be obtained often from measurement of the variation of their scattering intensity as a function of angle.

The analytical ultracentrifuge, of the type manufactured by Beckman Instruments, Inc., includes capabilities more extensive than the disk centrifuges discussed earlier. Because they can achieve far greater speeds, up to 60,000 revolutions per minute, they are able to separate far smaller particles. Indeed, one of the main applications of such systems is for the study of proteins. Such molecules are distinguished by their small size, rarely exceeding a few nanometers, and their associated greater diffusion coefficients. The determination of molecular weight, shapes, sizes, distributions and purity may, in principle, be derived directly from careful measurements of various features of a sedimenting sample. Such measurements include the need to observe and detect sharp boundary regions in the separating samples. The analytical ultracentrifuge relations used to derive molar mass, for example, are quite different from Eq. (1) used to derive the diameter of the separated particles. Rather than make assumptions concerning the molecule's shape and that Stokes' law describes the viscous drag force, the frictional force is assumed to be of the form $F_f = -fu = -f\, dR/dt = -f\dot{R}$, where f is the so-called frictional coefficient which depends on the particle's size and shape. The particle mass m is expressed in terms of its associated molar mass M by dividing by Avogadro's number $N_a$, i. e. $m = M/N_a$. Thus Eq. (2) is generalized to the form $$\frac{M}{N_a}\omega^2 R - \frac{M}{N_a}\bar{v}\rho_f \omega^2 R - f\dot{R} \approx 0, \quad (8)$$

where a steady state has been assumed to exist, i. e. $\ddot{R} \approx 0$. The second term in Eq. (8) corresponds to the contribution of buoyancy, where $\rho_f$ is the density of the solvent and $\bar{v}$ is the volume in g/mL displaced by each gram of the molecule. This value is often difficult to establish accurately. Combining the terms of Eq. (8) results in $$s = \frac{\dot{R}}{\omega^2 R}, \quad (9)$$

where $s = \frac{M}{N_a}[1 - \bar{v}\rho_f]$ is the sedimentation coefficient. For relatively sharp and symmetrical sedimenting boundaries, the sedimentation coefficient is obtained by integrating $$\frac{\dot{R}}{\omega^2 R}$$

to yield $$\ln(R/R_m) = s\omega^2 t, \quad (10)$$

where R is the boundary midpoint and $R_m$ is the meniscus position. Note the similarity of Eq. (10) and the corresponding result for the disk centrifuge of Eq. (7). A plot of $\ln(R)$ versus t yields a straight line of slope $\omega^2 s$ from which s may be calculated. Next, measurement of the rate of boundary spreading can be used to calculate the diffusion coefficient D that will depend on the effective size of the diffusing molecules through the corresponding frictional co-efficient f. Thus $$D = \frac{\Re T}{N_a f}. \quad (11)$$

The absolute temperature is T and $\Re$ is the gas constant. Taking the ratio of the sedimentation to the diffusion coefficient using Eq. (9) and (11) gives the molar mass $$M = \frac{s^0 \Re T}{D^0(1 - \bar{v}\rho)}. \quad (12)$$

The superscripts indicate that the calculated diffusion and sedimentation coefficients have been extrapolated to zero solute concentration. Each is generally calculated from measurements made using solutes at different concentrations.

The derivation of molar mass results based on Eq. (12) involves both a great amount of time and extensive calculations. The determination of the partial specific volume $\bar{v}$ itself is generally no trivial matter. Indeed, the determination of molar mass, though absolute, is most difficult to measure by analytical ultracentrifuge. The preferred method by which molar mass is determined using the analytical ultracentrifuge is by means of the technique of sedimentation equilibrium. A small volume of an initially uniform solution is centrifuged at lower speeds than generally required to obtain the molar mass by means of the sedimentation velocity method of Eq. (12). This results in a concentration gradient building up from the bottom of the cuvette. The molecular diffusion increases with increasing concentration so that there are two counter flows at each concentration: a radial flow caused by the centrifugal force and an opposite flow due to diffusion. Eventually an equilibrium concentration distribution is achieved where the concentration of the molecular species varies exponentially with $R^2$. For a monodisperse non-associating molecular solute, the molar mass may be shown to be $$M = \frac{2\Re T}{(1 - \bar{v}\rho)\omega^2} \frac{d(\ln c)}{d(R^2)}. \quad (13)$$

Thus a plot of ln c versus $R^2$ yields a slope directly proportional to the molar mass, M. Alternatively, by fitting the data of c versus $R^2$ to an exponential using a least squares' fit, one should be able to derive an estimate of $M(1 - \bar{v}\rho)$ directly.

Despite the great difficulties associated with finding molar masses directly using the analytical ultracentrifuge, the power of the instrument to separate such small molecules while at the same time being able study a wide range of other phenomena such as heterogeneity, association reactions, and a variety of thermodynamic properties make the analytical centrifuge a most useful analytical tool. Because the Beckman device measures concentration directly, when the instrument is combined with the MALS elements of the present invention, its utility is enhanced significantly. Thus molar masses may be calculated directly by combining concentration measurements with the absolute measurement of light scattered by the samples being studied. Once molar masses are so obtained, more accurate values of both sedimentation and diffusion constants may be derived almost effortlessly. The means by which the preferred embodiment of the present invention may be applied to the analytical ultracentrifuge will now be discussed.

Figures 5A, 5B:
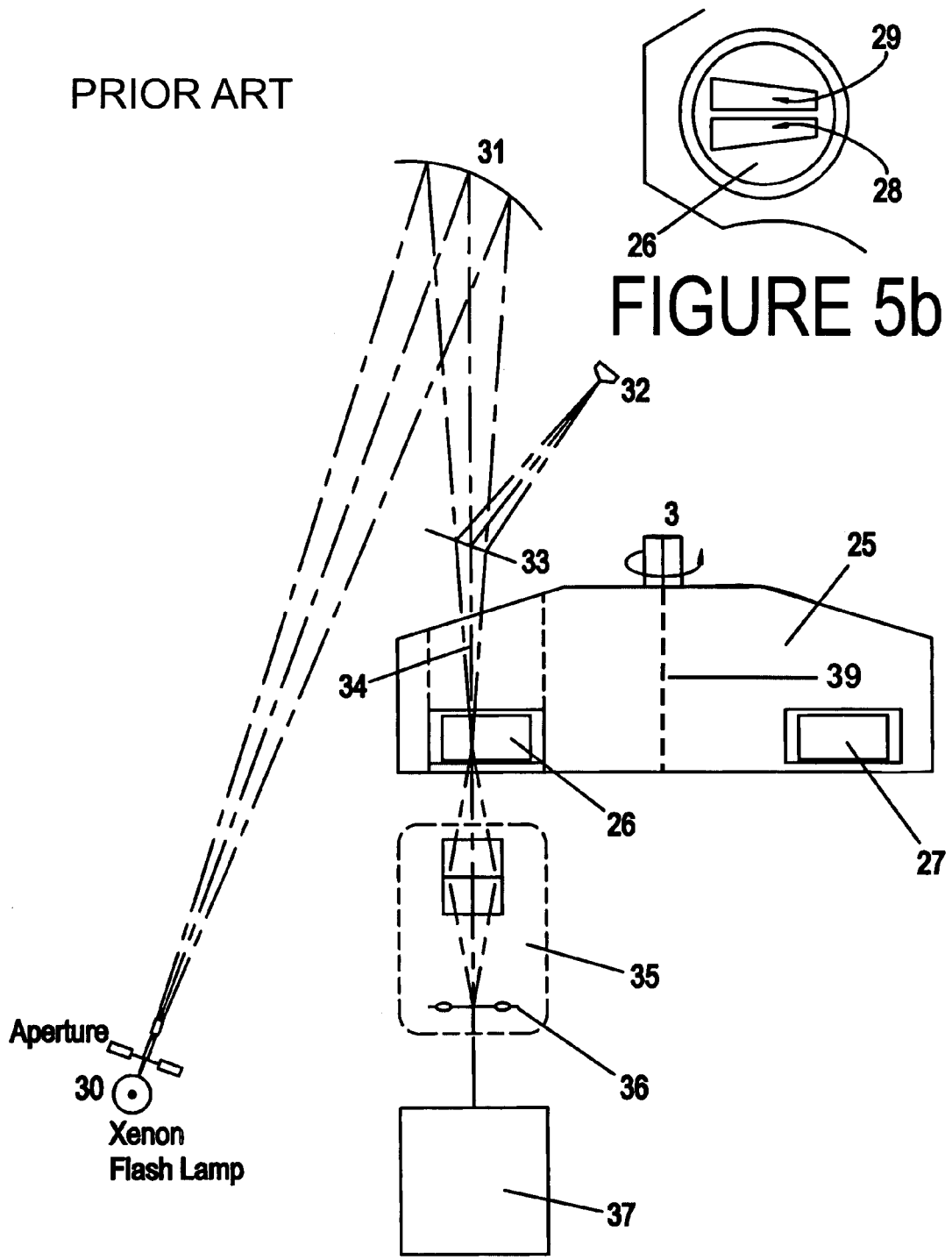
FIG. 5 is a schematic layout of the prior art optical system for the Beckman Optima XL-A Analytical Ultracentrifuge.

FIG. 5a presents a schematic of the optical system of the Beckman analytical ultracentrifuge. The sample holding rotor 25 rotates about shaft 3 within an evacuated chamber. Similar to the Horiba structure of FIG. 5a, the rotor contains sample and reference cuvettes. However, two pairs are included at diametrically opposite locations 26 and 27. FIG. 5b shows a top view of one of these locations, for example 26, containing sample 28 and reference 29 cuvettes. By this means, two distinct samples may be processed during each experiment. Note that each cuvette is constructed with a side boundary lying along a radius at a slight angle to the other side that lies along the principal diameter of the rotor. This structure helps reduce internal sample streaming during separation. A Xenon flash lamp source 30 is shown together with a steering diffraction grating 31 and incident light monitor 32 that receives a small signal proportional to the incident intensity by means of a beam splitter 33. The focused beam 34 passes sequentially through the sample and reference cells when cell-containing regions 26 or 27 are in the beam. These cells lie at the variable radial distance 39 from the axis of rotation 3. In general, the incident light source is pulsed so that the beam is on only during its passage through the sample or reference cells. The diffraction grating permits also the selection of the wavelength of the incident beam 34 over the range of wavelengths associated with the light source; in this case, a Xenon lamp. Generally, wavelengths in the near ultraviolet are selected as a great many studies with such apparatus involve proteinaceous materials that absorb strongly in the UV. An optical imaging system 35 collects light transmitted through the sample pairs within 26 or 27 from a small radial region within the sedimenting sample. The image of the mask 36 at the illuminated sample defines this narrow field of view. A photodetector such as a photomultiplier tube 37 detects this transmitted light, though other detector devices such as photodiodes may be employed.

Figure 7:
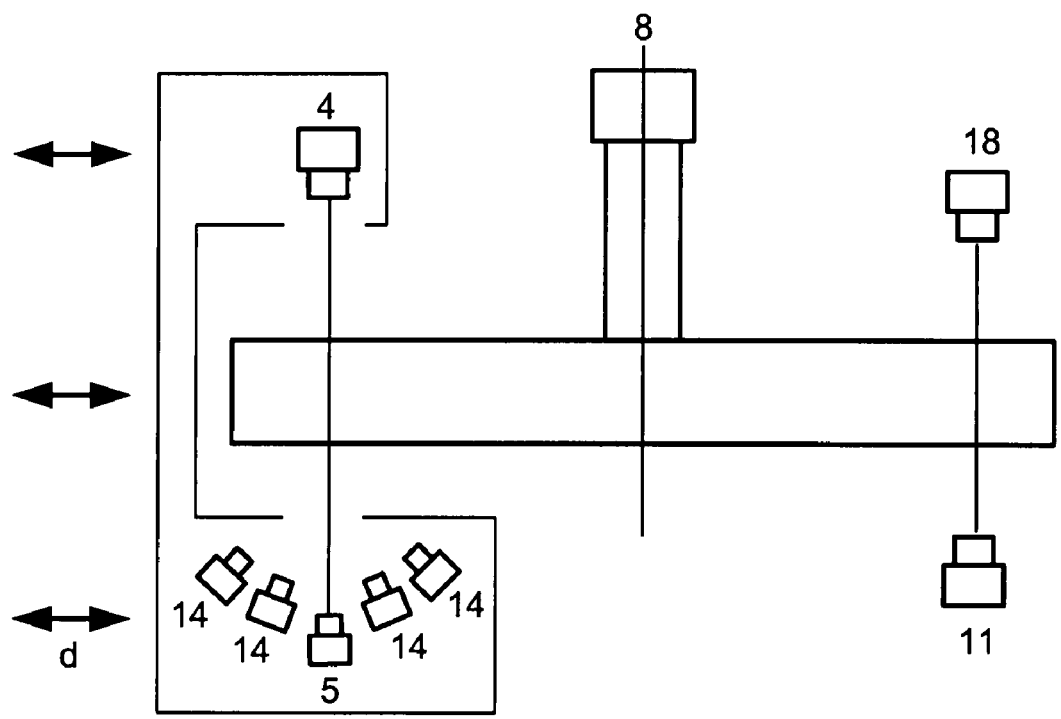
FIG. 7 shows an integrated light source/detector system capable of radial scanning while preserving the relative orientations of the translatable elements.

The structure comprised of the beam 34, imaging system 35, and photodetector 37 are controlled to move in the radial direction as a unit permitting, thereby, the sample to be measured at different radial distances. For the disk centrifuges, on the other hand, the beam/detector pair is set traditionally at a single radial distance throughout the entire measurement. The preferred embodiment of the present invention, however, permits this radial distance to be variable for all forms of centrifuge, as to be shown in FIG. 7 presently. Depending upon the types of particles/molecules to be separated, the radial scans are repeated many times to yield a sedimentation profile as a function of time. In the preferred embodiment of this invention, when elastically scattered light measurements are implemented, a second light source 4 is added. It will move preferably in parallel with source 30 and be located in the same plane 180° after it. The source will preferably be a laser producing a fine beam 12. Although the radial scanning of the sample by this second beam 12 may be in parallel with the scanning by the UV beam 34, the radial scanning rates of the two sources may be different. The laser source may be pulsed as well. In general the fine laser beam will be of diameter between a few millimeters to a few micrometers, though a diameter of the order of 100 μm would be used in a preferred embodiment.

Figure 6:
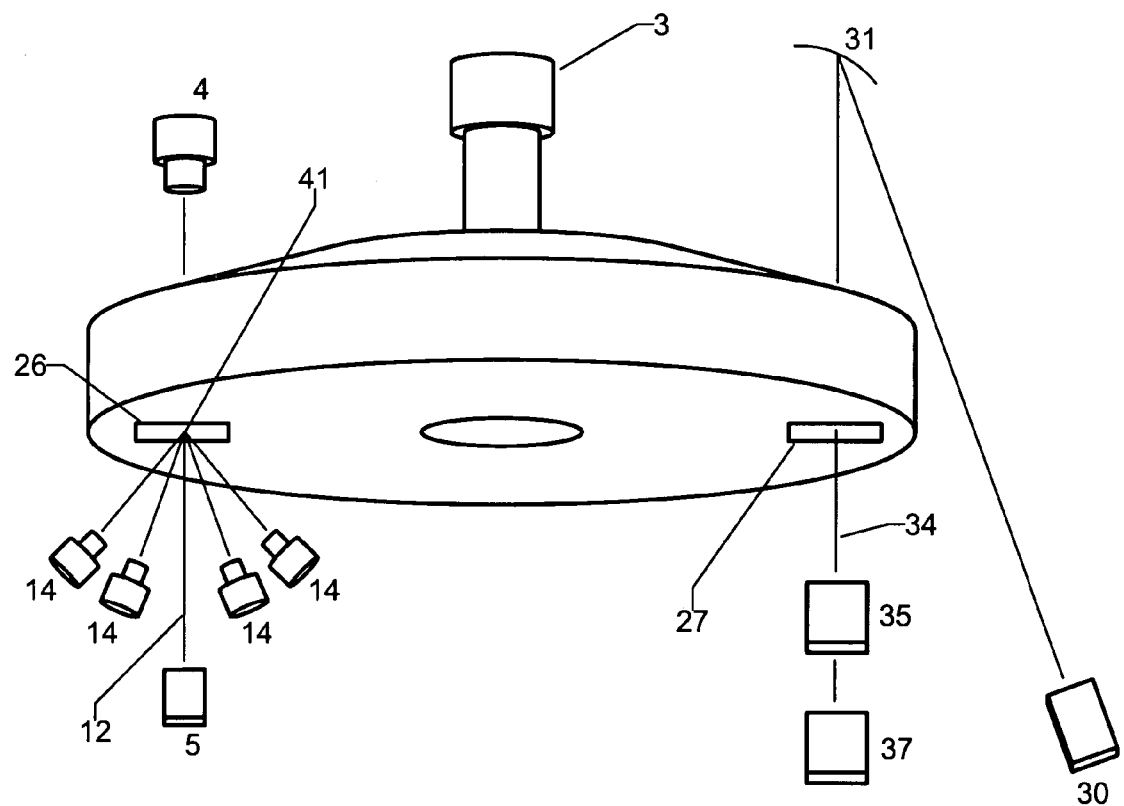
FIG. 6 shows a preferred embodiment of the illumination and detection system shown in FIGS. 3 or 4 as implemented for the Beckman Analytical Ultracentrifuge.

FIG. 6 shows an instantaneous cross sectional view of the preferred embodiment for an analytical ultracentrifuge. Shown are the imaging system 35 and the photomultiplier detector 37 of the Prior Art structure of FIG. 5a. This primarily UV source producing beam 34 and associated detector 37 will permit determination of the intersected sample's concentration as required. An independent, usually laser-based illumination system discussed above includes the laser 4 producing the beam 12 passing through the sample and reference cuvettes, located in pairs at 26 and 27, sequentially and exiting at 41 and then entering a forward monitor 5. In the region between 41 and 5 are a set of collimated scattered light detectors 14 similar to the detectors of FIGS. 3 and 4b. These detectors, as well as those shown in FIGS. 3 and 4b, generally lie in a plane and intercept scattered light from the small illuminated volume 16 within the sample and reference cuvette/cell pair located in cavity 26 or 27. The detectors move with the other elements of the laser system and collect scattered light throughout the radial scanning, d, transverse to the plane of the figure. If the incident laser is plane polarized, as is generally the case, the detectors are constrained to lie in a plane perpendicular to the laser's plane of polarization. Thus the sample particle mass and size distribution profiles throughout the scanned cuvettes may be determined from the scattering measurements and recorded by the two illumination beams of the inventive system described. Accordingly, all detection, light sources, and optical elements may be attached to a single fixed platform relative to the rotor 3 or on two separate platforms: one for the conventional UV source optical system and a second for the laser baser scattered light detection system. The platform, or platforms, may move radially, permitting, thereby, the radial scanning capability of the traditional analytical ultra centrifuge as well as the additional scattered light detection capability of the present inventive structure. When the reference cuvette 29 arrives at the position previously occupied by the sample cuvette 28, light scattered by its solution will be collected in a similar manner. Both for the light scattering implementation and the conventional absorbance, the difference of these two signals is used for the subsequent analyses.

The two light sources producing beams incident upon the sample and reference cuvettes will originate from the laser source 4 or the variable UV/visible light source 30 as are conventional, for example, in the analytical ultracentrifuge. In FIG. 6, the laser source 4 used to produce a light beam 12 to interrogate the sample is shown mounted in juxtaposition to the steering diffraction grating 31. Both produce beam's 12 and 34, respectively, which intersect the sample and reference cuvettes at the same radial distance, but displaced 180° in rotation angle. The UV source beam 34 from the Xenon flash lamp 30 will strike the cuvette after the incident the laser beam 4 has passed through it as the cuvette rotates counterclockwise through the same radial position with respect to the cuvette-contained separating reference 27 and sample 26. The corresponding transmitted UV/visible light beam 34 intensity, used to calculate the sample absorption, and the light scattered from laser beam 4 into detectors 14, are combined to calculate the particle/molecule size and mass. The signals from the UV and laser beam interactions with the sample are collected sequentially at the same radial position of the sample.

Alternatively, for the analytical ultracentrifuge, the laser beam may be arranged to be collinear with a UV/visible light source, or to replace it if the determination of the molar mass using concentration detection means is not required. A multiwavelength laser or light source may be selected as well, with various filters chosen to select the transmitted beam wavelength. Still other filters may be selected and attached to the scattered light detectors to eliminate detection of specific scattered wavelengths. There are many other means for providing such beams, as would be obvious to those skilled in the art of optical design FIG. 7 presents a schematic illustration of a MALS implementation whose radial position may be varied by the system operator. The incident light source 4, light trap 5 and scattered light detectors 14 are all mounted on a single structure capable of radial movement while preserving the relative spatial orientations of the attached elements. Although such simultaneous motion of the key elements referenced might be achieved by synchronizing the motions of two or more platforms each holding only one or two elements, the preferred embodiment of the invention would affix all elements to a single radially translatable structure. In this manner, all elements will maintain their relative orientations most easily.

The dual light source implementations discussed above, whereby the sample is illuminated sequentially by the two different light sources as the sample containing region rotates past them, is implemented as well in the disk centrifuge geometries discussed earlier. This dual sequential illumination is illustrated with the structures of FIGS. 3, 4b, and 6. Indeed, multiple illumination sources may always be used for any of the centrifugal separation devices. Such multiple sources are not restricted to two, nor is a minimum of two required If the laser and UV/visible light sources are superimposed to form a single incident beam, then the scattered light detectors 14 would be fitted preferably with narrow band pass filters to remove UV/visible light scattered by the solutions. Such filters would be preferably interference filters permitting only elastically scattered light at the laser wavelength to be detected. If inelastically scattered laser light, such as fluorescence, is to be detected the corresponding detector filters would be selected accordingly. If any of the light sources employed is polarized, polarization sensitive analyzers may be attached to selected scattered light detectors to permit quantitative measurement of depolarization scattering effects. These same comments apply as well to all centrifuge separation devices.

It is clear from the discussions above that the key elements of this invention apply equally to various types of instrumentation using photometric means to monitor sedimentation phenomena induced by an applied centrifugal force. The basic objective of the present invention is to enable measurement of scattered light from regions of the sample being separated by such means. From such measurements made over a range of scattering angles, it becomes possible to derive particle size directly, irrespective of diffusion phenomena. For the case of separated sub-micrometer particles, means by which such scattered light measurements may be used to measure particle size and size distributions has been explained in such papers as:

"Absolute Measurement of Diameter Distributions of Particles Using a Multiangle Light Scattering Photometer Coupled With Flow Field-Flow Fractionation," D. W. Shortt and D. Roessner, and P. J. Wyatt, Am. Lab. 17, 21 (1996); and "Submicrometer particle sizing by multiangle light scattering following fractionation," P. J. Wyatt, *J. Colloid and Interface Science* 1979, 9-20 (1998).

As has been repeated frequently, for the case of solvated molecules undergoing separation by centrifugal means, the weight average molar mass may be derived directly if the concentration of the molecules is known in addition to the differential refractive index increment, dn/dc. Details of such quantities may be found in the U.S. Pat. No. 6,651,009 by Trainoff and Wyatt referenced at the beginning of this specification as well as the reference by Wyatt discussed in the following paragraph. Most centrifugal separation devices, and certainly the analytical ultracentrifuge, use a light beam whose absorption by the solution may be used directly to calculate the concentration of the molecules present. Thus for the case of solvated molecules, a UV/visible light source is often sufficient as it exists to produce the absorption measurement sufficient to determine, from the sample's extinction coefficient, the molecular concentration. For larger particles, on the other hand, such absorption techniques rarely may be used to calculate the particle concentration because of the role played by the particle scattering. In addition, the angular variation of such particle scattering is generally sufficient to calculate the effective particle size. Since the forward transmitted beam that passes directly through the sample is useful to determine the molecular concentration and, perhaps for some particles, the beam transmittance, the preferred embodiment of the invention would continue the use of such measurements. If the particle structure is known, then from the MALS measurement, it is possible to determine the actual differential particle number distribution from the centrifugally-fractionated sample following the methods described by the applicant in his U.S. Pat. No. 6,774,994.

The ability to measure molecular mass and size directly for samples undergoing ultracentrifuge separation, and especially for proteins, is a particularly significant application of this invention as it potentially eliminates those elements most difficult to measure from conventional analytical ultracentrifugal analysis. Most important among such elements is the determination of the volume of solvent displaced by the molecule whose mass and size is to be determined. Once the concentration and light scattering response as a function of scattering angle of a particular molecular species are known, the molecular mass may be determined immediately following the methods described in detail by Wyatt in his 1993 Analytica Chimica Acta paper in volume 271, pages 1 et seq.; entitled "Light Scattering and the Absolute Characterization of Macromolecules." Once the mass of a separating species has been so-determined, the molecules' volume, for example, may be calculated explicitly from the sedimentation coefficient derived via Eq. (10). Such determinations have never been made directly in this manner. The implications of these direct determinations for the protein chemistry and related fields are of great importance.

Another key element of the invention relates to the modifications at the exit surfaces of the sample-containing regions. As the beam leaves the sample, it is generally expected to exit normal to the transparent region in which the sample is restricted. Thus the normal surface through which the undeviated incident beam passes remains the same as that currently employed in such centrifugal separation devices. However, there is no reason to require the beam to intersect normally. If space permits, the beam could be incident at a different angle, permitting thereby a larger range of scattering angles to be detected. The surface could also be made concave as described in the earlier parent application. As has been mentioned previously, the invention is intended to permit measurement of light scattered over a range of scattering angles from a small volume within the illuminated sample. The collimation of the scattered light detectors defines the field of view, i. e. the transverse dimension of the illuminated scattering volume from which scattered light may be detected. For all of the centrifuge implementations, it is desirable also to reduce stray light by whatever means possible. Antireflection coating of all air/glass surfaces through which light beams may travel is one of the most obvious first courses of action.

In order to process all detected signals, including the scattered light signals, for subsequent analyses, such analog signals are traditionally converted into digital representations which are then stored within memory means for later processing by computer means. Such data collection, conversion, and subsequent processing are standard features of most analytical instrumentation. The means by which such data are used to derive particulate properties such as size, mass, and their distributions are found extensively in the literature. The earlier references to Wyatt's 1993 Analytica Chimica Acta article, as well as his numerous papers and patents cited in this specification, describe many of these means and procedures.

In summary, in order that a scattered light measurement be made from a sample undergoing separation due to the application of centrifugal forces thereon, the sample must be contained in a holder that is made to be an integral part of the centrifuge rotor. This sample holding region must have at least two transparent surfaces each of whose normal lies parallel to the centrifugal axis of rotation, permitting, thereby, an external light beam to pass through said sample as it rotates in a circular path therethrough. The incident light beam enters the sample holding region through a first transparent surface, then it passes through the sample, and then exits through a second transparent surface; the sample being contained between said two transparent surfaces. For the disk centrifuge of FIG. 1, the transparent sides are the two sides of the cylindrical cavity. For the analytical ultracentrifuge of FIG. 5 and the disk centrifuge of FIG. 4, the samples are contained in discrete cuvettes. But all such sample holding means are effectively equivalent as they constrain the sample to lie between two transparent surfaces through which a fine light beam may pass at varying radial distances from the axis of rotation. As the samples separate under the influence of the applied centrifugal forces, the impinging beams will sample different types of particles depending upon their physical properties responsive to the applied forces and the radial distance of the from the axis of rotation.

The addition of a MALS detection capability to a centrifuge separator permits the derivation of the illuminated particle sizes by measuring the intensity variation of the detected scattered light as a function of scattering angle. In addition, if the particles are molecules such as proteins, their weight average molar mass may be determined if their concentration is known also at the same illuminated region from which the scattered light originates. For the case of proteins, this becomes particularly easy to measure by the introduction of a UV light source at the same radial distance as the illuminated scattering volume. From knowledge of the protein's associated extinction coefficient at the wavelength of the illuminating UV source beam, the total beam path length through the sample, and the attenuation of the UV beam through the sample, the protein concentration is calculated.

Finally, as mentioned frequently earlier, the best light source for making MALS measurements is certainly a laser producing a fine light beam. For such light sources, it is preferable that the beam be plane polarized in a plane perpendicular to the plane about the sample in which lie the detectors. At times it may be desirable to measure scattered light outside a single plane in which case some detectors may not lie perpendicular to the plane of polarization.

Although it is usual that the single light source of a conventional AUC be able to move in the radial direction during the centrifugal separation permitting thereby that the sample be repeatedly radially scanned, this same feature is easily implemented for both the UV source as well as the scattered light source in each of the centrifuge structures earlier discussed.

As will be evident to those skilled in the arts of light scattering, there are many obvious variations by which means one may incorporate into a centrifugal separation device the detection of light scattered over a broad range of scattering angles. The actual geometry of the particular centrifugal separator may limit or expand these possibilities. Thus, for example, the discrete detectors illustrated throughout this disclosure may be replaced by collections of detectors such as CCD arrays as well as photomultiplier tube arrays and micro channel plate arrays. The enhancements that such multiangle scattered light detectors add to centrifugal separators are many as I have described and implied in my invention and do not depart from the fundamental elements that I have listed for their practice; all such variations are but obvious implementations of my invention described hereinbefore and are included by reference to my claims, which follow.

The invention claimed is:

1. A method to characterize a solution of small particles comprising the steps of
   a) placing an aliquot of said solution into a transparent containment means integrated into a centrifugal rotator means where said containment means
      i. provides visible access to said aliquot through transparent walls therein and
      ii. includes a range of radial distances with respect to said centrifuge axis of rotation through which said particles in said aliquot may move during said separation;
   b) activating said centrifugal rotator to rotate about its axis of rotation producing, thereby, a centrifugal force acting on said particles in said aliquot;
   c) illuminating a region of said aliquot through said transparent containment means by a fine beam of light wherein
      i. said light beam intersects said solution at predetermined radial distance from said axis of rotation
      ii. said beam enters through one transparent containment wall and exits through another, with said aliquot contained therebetween, as said solution passes through said fine light beam;
   d) detecting light scattered by said aliquot from said incident fine beam of light, at selected time intervals, at a plurality of angular directions thereto by a corresponding plurality of detector means each of which is collimated and so-arranged to collect light only scattered into a specific direction subtending a finite defining solid angle, and each detector producing from said detected scattered light an electrical signal e) converting said electrical signals into digital representations thereof and storing in memory means for subsequent processing; and f) processing said digital representations of said scattered light signals and said transmitted beam signal to derive therefrom characteristics of said small particles in said aliquot.

2. The method of claim 1 where a second light source produces a second fine light beam that illuminates said aliquot subsequent to said first fine beam at the same radial distance therefrom but at a different angular location on said rotor as said rotor moves said transparent containment means through said second light beam; said second fine light beam entering a detector after passage through and exiting from said aliquot.

3. The method of claim 2 where said second light source produces a fine beam of light permitting thereby said detector of said beam emerging after passage through said aliquot to produce a signal representative of the concentration of said particles through which said second fine beam passes.

4. The method of claim 3 where said second light source produces said fine beam at an ultraviolet wavelength.

5. The method of claim 1 where said light source and plurality of detectors may move in unison radially so as the permit said light beam to sample different radial regions of said contained aliquot and said plurality of detector means to detect light scattered from said corresponding different radial regions.

6. The method of claim 1 where said centrifugal rotator means is a component of a disk centrifuge.

7. The method of claim 1 where said centrifugal rotator means is a component of an analytical ultracentrifuge.

8. An apparatus to characterize a solution of small particles comprising a) a sample holding means integrated into a centrifugal rotator means where said containment means
  i. extends over a range of radial distances with respect to said axis of rotation,
  ii. incorporates transparent walls containing an aliquot of said solution therebetween;

b) a light source means providing a fine beam of light that passes through said transparent walls when said holding means lies in the path of said fine beam of light while said solution aliquot undergoes separation due to the centrifugal forces impressed thereon by rotation in a circular path about said axis;

c) a forward transmitted light beam trapping means into which said fine beam of light enters after traversing said transparent aliquot-containing region;

d) a plurality of detector means, arranged about said transmitted light beam at varying angles therefrom, with each detector means so-arranged to collect light scattered from the same region of said aliquot illuminated by said incident fine beam of light passing through said transparent sample holding means, at a specific angular direction and into a corresponding solid angle subtended thereby; and e) electronic means to convert signals from said scattered light detectors successively in time into digital representations, and process said digital representations to derive therefrom characteristics of said small particles in solution.

9. The apparatus of claim 8 that includes a second light source producing a second fine beam of light illuminating said sample subsequent to said first fine beam at the same radial distance therefrom but at a different angular location on said rotor as said rotor moves said sample holding means into said second light beam.

10. The apparatus of claim 9 where said second light source produces a fine beam of an ultraviolet wavelength permitting thereby the component of said beam emerging after passage through said sample to represent a measure of the concentration of said particles through which said second fine beam passes.

11. The apparatus of claim 9 where said centrifugal rotator means is a component of a disk centrifuge.

12. The apparatus of claim 9 where said centrifugal rotator means is a component of an analytical ultracentrifuge.

13. The apparatus of claim 8 where said light source and plurality of detectors may move in unison radially so as the permit said light beam to sample different radial regions of said contained sample and said plurality of detector means to detect light scattered from said sample at said corresponding different radial regions.

* * * * *